US007892532B2

(12) United States Patent
Titus et al.

(10) Patent No.: US 7,892,532 B2
(45) Date of Patent: Feb. 22, 2011

(54) INTRACELLULAR DELIVERY OF OSTEOINDUCTIVE PROTEINS AND PEPTIDES

(75) Inventors: Frances Louisa Titus, Atlanta, GA (US); Jeffrey C. Marx, Germantown, TN (US); Scott D. Boden, Atlanta, GA (US); Sangwook T. (Tim) Yoon, Atlanta, GA (US); Susan Drapeau, Cordova, TN (US)

(73) Assignee: Warsaw Orthopedic, In Emory University

( * ) Notice: Subject to any disclaimer, the term of this patent is extended or adjusted under 35 U.S.C. 154(b) by 276 days.

(21) Appl. No.: 10/806,915

(22) Filed: Mar. 23, 2004

(65) Prior Publication Data

US 2004/0197867 A1 Oct. 7, 2004
US 2008/0166755 A9 Jul. 10, 2008

Related U.S. Application Data

(63) Continuation-in-part of application No. PCT/US00/11664, filed on Apr. 28, 2000, application No. 10/806,915, which is a continuation-in-part of application No. 09/959,578, filed on Jun. 21, 2002, now Pat. No. 7,045,614.

(60) Provisional application No. 60/456,551, filed on Mar. 24, 2003, provisional application No. 60/132,021, filed on Apr. 30, 1999.

(51) Int. Cl.
*A01N 63/00* (2006.01)
*C12N 5/00* (2006.01)
*C12N 15/00* (2006.01)

(52) U.S. Cl. ............... 424/93.21; 435/455; 435/325

(58) Field of Classification Search .......... None
See application file for complete search history.

(56) References Cited

U.S. PATENT DOCUMENTS

| | | | |
|---|---|---|---|
| 5,580,775 A | 12/1996 | Fremeau, Jr. et al. | |
| 5,652,122 A | 7/1997 | Frankel et al. | |
| 6,300,127 B1 | 10/2001 | Hair et al. | |
| 6,444,803 B1 | 9/2002 | Hair et al. | |
| 6,475,516 B2 | 11/2002 | DiCosmo et al. | |
| 6,521,750 B2 * | 2/2003 | Hair et al. ............ | 536/23.5 |
| 6,858,431 B2 * | 2/2005 | Hair et al. ............ | 435/455 |
| 2003/0180266 A1 | 9/2003 | McKay et al. | |
| 2003/0225021 A1 | 12/2003 | McKay et al. | |

FOREIGN PATENT DOCUMENTS

WO WO99/06563 * 2/1999

OTHER PUBLICATIONS

Boden et al. (Endocrinology 1998, vol. 139, No. 12, pp. 5125-5134).*
van Beuningen et al. (Osteoarthritis and Cartilage, 1998. vol. 6, pp. 306-317).*
Liu et al. Overexpressed LIM mineralization proteins do not require LIM domains to induce bone. J Bone Miner Res. Mar. 2002;17(3):406-14.*
U.S. Appl. No. 09/959,578, filed Jun. 21, 2002, Boden et al.
Fujihara, S., et al., Inhibition of NF-kB by a Cell Permeable Form of IκBα induces apoptosis in eosinophils, *BBRC*, 326:632-637 (2005).
Porter, T., et al., Biomolecules in Tissue Engineered Medical Products (TEMPs): A Case Study of Recombinant Human Bone Morphogenetic Protein-2 (rhBMP-2), *Journal of ASTM International*, Jan. 2004, 1(1):1-21.
Boden, et al., "Adenoviral Delivery of LMP-1 Induces Consistent Spine Fusion," 47th Annual Meeting, *Orthopaedic Research Society*, San Francisco, California (2001).
Nagahara, et al., Transduction of full-length TAT fusion proteins into mammalian Cells: TAT-p27[Kip1] Induces Cell Migration, *Nature Medicine*, 4(12):1449-1452 (1998).
Southern, et al., "Detection of Specific Sequences Among DNA Fragments Separated by Gel Electrophoresis," *J. Mol. Biol.*, 98:503-517 (1975).
Alwine, et al., "Detection of Specific RNAs or Specific Fragments of DNA by Fractionation in Gels and Transfer to Diazobenzyloxymethyl Paper,"*Meth. Enzymol.*, 68:220-242 (1979).
Sambrook, et al., "Extraction of RNA with Guanidinium Thiocyanate Followed by Centrifugation in Cesium Chloride Solutions," Molecular Cloning: A Labortory Manual, 2nd ed., *Cold Spring Harbor Press*, 7.19-7.50 (1989).
Heldin, et al., "TGF-β Signalling from Cell Membrane to Nucleus through SMAD Proteins," *Nature*, 390:465-471 (1997).
Lin, et al., "Inhibition of Nuclear Translocation of Transcription Factor NF-κB by a Synthetic Peptide Containing a Cell Membrane-permeable Motif and Nuclear Localization Sequence," *J. Biol. Chem.*, 270(24):14255-14258 (1995).
Rojas, et al., "Genetic engineering of proteins with membrane permeability," *Nat. Biotech.*, 16:370-375 (1998).
Fawell et al., "Tat-mediated delivery of heterologous proteins into cells," *Proc. Natl. Acad. Sci. USA*, 91:664-668 (1994).
Schwarze, et al., "Protein Transduction: Unrestricted Delivery into all Cells," *Trends in Cell Biology*, 10:290-305 (2000).
Jiang, et al., "Pluripotency of Mesenchymal Stem Cells Derived from Adult Marrow," *Nature*, 418:41-49 (2002).
Viggeswarapu, et al., "Adenoviral Delivery of LIM Mineralization Protein-1 Induces New-Bone Formation in Vitro and in Vivo,"*J. Bone Joint Surg.*, 83(3):364-376 (2001).
Xiaoqing Guo, et al., "Transduction of Functionally Active TAT Fusion Proteins into Cornea," *Experimental Eye Research*, vol. 78, pp. 997-1005 (2004).
Michelle Becker-Hapak, et al., "TAT-Mediated Protein Transduction into Mammalian Cells," *Methods*, vol. 24, pp. 247-256 (2001).
Jeffrey L. Wrana, "Crossing Smads,"*Science's Stke*, vol. 23, pp. 1-9 (2000).

(Continued)

Primary Examiner—Michele K Joike

(57) ABSTRACT

The invention provides fusion polypeptides comprising protein transduction domains and osteoinductive polypeptides, as well as methods of using such polypeptides to induce osteogenesis and to promote proteoglycan synthesis. The invention also provides osteoinductive peptides which have demonstrated the ability to induce bone formation in vivo.

22 Claims, 6 Drawing Sheets

OTHER PUBLICATIONS

Kristin A. Waite, "From Developmental Disorder to Heritable Cancer: It's All in the BMP/TGF-β Family," *Nature Reviews*, vol. 4, pp. 763-773 (2003).

Rik Derynck, et al., "Smad-dependent and Smad-independent Pathways in TGF-β Family Signalling," *Nature*, vol. 425, pp. 577-584 (2003).

Patricia Ducy, et al., "The Family of Bone Morphogenetic Proteins," *Kidney International*, vol. 57, pp. 2207-2214 (2000).

Douglas Hanahan, et al., "The Hallmarks of Cancer," *Cell*, vol. 100, pp. 57-70 (2000).

\* cited by examiner

Fig. 4

| Experiment No. | Rat #13 | Rat #20 | Rat #29 |
|---|---|---|---|
| Experiment Date | April 11, 2002 | June 13, 2002 | September 5, 2002 |
| TAT-LMP | | | |
| Prep Date | 3/7/02 | 3/7/02 & 6/7/02 | 8/30/02 |
| Stock | PBS | PBS & Ethanol | KOH |
| Recovery | | 80% | |
| Specifics | | | Lypophilized |
| ID# | Rabbit #1448 | Rabbit #2013 | Rabbit #2015 |
| WB (vol) | 15 ml | 15 ml | 12 ml |
| BC Prep | Manual-GH | Manual-GH | Manual-GH |
| Incubation by: | MN | MN | MV |
| Time: | 30 min. | 30 min. | 30 min. |
| Vol. Total: | 110-120 µl | 105-110 µl | 109 µl |
| Cells/vol. | 15 M/ml | 15 M/ml | 9.1 M/ml |
| Cell#/disc | 1.5 M | 1.5 M | 1 M |
| Col. Lot# | 11/26/01 | 1/22/02 | 6/14/02 |
| Doses Tested | 1.56, 3.1, 6.3, 12.5, 25, 50, 100 & 200 nM | .16, .31, .63, 1.25, 1.56, 2.5, 5, 10 nM | 0.08, .16, .31, .63, 1.25, 2.5, 5, 10 nM |
| Results | Bone Made: 1.56 nM* (3 of 4) | Bone made: .625 & 1.25 nM** (4 of 4) *did not repeat | Bone made: 10 nM (2 of 3), 5, 2.5, 1.25 nm (4 of 4) |
| BMP-2 | Yes | Yes | Yes |
| Miscellaneous | | | Lypophilizing process differed from batch 8/1/02 used in Rat #27 |

Fig. 5

| Experiment No. | Rabbit #13 | Rabbit #20 | Rabbit #29 |
|---|---|---|---|
| Experiment Date | July 16, 2002 | August 20, 2002 | September 3, 2002 |
| Prep Date | June 7, 2002 | June 7, 2002 | August 30, 2002 |
| Stock | Ethanol | Ethanol | KOH |
| Specifics | | | Lypophilized |
| ID# | Rabbits | Rabbits | Rabbits |
| WB (vol) | 6 ml | 6 ml | 6 ml |
| BC Prep | Manual-GH | Manual-GH | Manual-GH |
| Incubation by: | EG (MN) | MV | MV |
| Time: | 30 min. | 30 min. | 30 min. |
| Vol. Total: | 1050 µl | 1050 µl | 1050 µl |
| Cells/vol. | 6 M/ml | 6 M/ml | 6 M/ml |
| Cell#/disc | 6 M | 6 M | 6 M |
| | Helistat | Helistat | Helistat |
| Doses Tested | 2.5, 5, 10, 20, 30, 40, 50, 100 | 45, 50, 55, 60, 65, 70, 75 | 5, 10, 20, 30, 40, 50, 60, 70 |
| Results | Bone Made: 50 ng/M (3 of 3) Fusion = 2 of 3 | Bone Made: 50 ng/M (2 of 2) Fusion = 1 of 2 | Bone Made: 50 ng/M (3 of 3) & 60 ng/M (2 of 3) Fusion - 1/dose |

Fig. 6

| Peptide | Number of Positive Results (Bone Formation Detected) | Peptide Dose in nM | Observations |
|---|---|---|---|
| Peptide 1 (SEQ ID NO 1) | 2 | 5 | Some bone growth |
|  | 2 | 10 | Some bone growth |
| Peptide 2 (SEQ ID NO 2) | 1 | 10 | Moderate growth |
|  | 3 | 12.5 | Moderate to good growth |
|  | 1 | 11 | Palpable growth |
| Peptide 3 (SEQ ID NO 3) | 1 | 25 | Some bone growth |
| Peptide 4 (SEQ ID NO 4) | 2 | 17.5 | Good bone growth |
|  | 1 (palpable) | 15 | Palpable growth |
| Peptide 5 (SEQ ID NO 5) | 1 | 5.5 | Some bone growth in rabbit |
| Peptide 6 (SEQ ID NO 6) | 2 | 5 | Some bone growth |
|  | 2 | 10 | Some bone growth |
| Peptide 7 (SEQ ID NO 7) | 3 | 10 | Good bone growth (palpable) |
|  | 2 | 12.5 | Good bone growth (palpable) |
|  | 1 | 20 | Excellent bone growth (palpable) |
| Peptide 8 (SEQ ID NO 8) | 2 | 12.5 | Some bone growth (rat) |
|  | 1 | 5 | Some bone growth (rabbit) |

US 7,892,532 B2

INTRACELLULAR DELIVERY OF OSTEOINDUCTIVE PROTEINS AND PEPTIDES

This application claims the benefit of U.S. provisional application No. 60/456,551, filed Mar. 24, 2003. This application is a continuation-in-part application of PCT application PCT/US00/11664 filed on Apr. 28, 2000, which claims benefit of U.S. Provisional Application Ser. No. 60/132,021, filed on, Apr. 30, 1999. This application is also a continuation-in-part of U.S. application Ser. No. 09/959,578, filed Jun. 21, 2002 now U.S. Pat. No. 7,045,614, which claims the benefit of U.S. Provisional Application No. 60/132,021, filed on Apr. 30, [1997]1999.

FIELD OF THE INVENTION

The present invention relates generally to osteoinductive proteins and methods for the delivery of those proteins into cells. More specifically, the invention relates to osteoinductive proteins such as LIM mineralization proteins (LMPs), bone morphogenetic proteins (BMPs) and Smad proteins, conjugates of such osteoinductive proteins with protein transduction domains (PTDs), conjugates of PTDs and nucleic acids comprising nucleotide sequences encoding osteoinductive proteins, and to the transduction of these conjugates into cells. Furthermore, the invention relates to the use of PTD/osteoinductive protein conjugates to promote bone growth and disc regeneration.

BACKGROUND

Tissue regeneration is an important component of the healing process subsequent to disease, trauma, or surgery. In situations where disease or trauma produces bone defect, for example, or where a surgical procedure such as insertion of an autograft or allograft, bone bridge, or bone fusion is used to correct a bone defect, bone regeneration is a central goal of recovery. It is not, however, a goal that is always or easily achieved and much research has been devoted to newer and more effective ways to promote tissue repair and regeneration.

Elimination of joint motion by creation of a bone bridge is a common orthopedic strategy for the treatment of degenerative spine and joint disorders. Failure of spine fusion can occur in as many as forty-five percent of the patients who undergo the procedure, leaving them with continued pain, repeated surgeries, medical costs, and overall therapeutic failure.

Intracellular and extracellular osteoinductive proteins promote bone growth and repair and constitute potential targets for therapeutic use. Such proteins include the bone morphogenetic proteins and the LIM mineralization proteins. BMPs have been shown to stimulate bone growth in vivo and LMPs, particularly LMP-1 and LMP-3, have a more upstream effect on osteoinduction, as evidenced by the fact that inhibition of LMP-1 expression blocks nodule formation that would normally be stimulated by glucocorticoids or BMP-6. Since they are considered "extracellular" proteins, acting via interaction with cell surface receptors, very high doses of bone morphogenetic proteins are required to achieve consistent effects in humans. Since the manufacturing costs of BMPs is generally high, this can mean that the cost of therapy is prohibitive. Therefore, although BMPs have demonstrated efficacy and are a viable therapeutic aid to osteoinduction, it would be beneficial to develop an alternate therapy that might be more cost-effective and possibly even more therapeutically effective.

Delivery of LMPs to the intracellular environment provides an attractive therapeutic regimen. This can be accomplished by transfection of cells with plasmids comprising a nucleotide sequence encoding a LIM mineralization protein, or can be done by infection of target cells with a viral vector carrying the nucleotide sequence of LMP. Each of these techniques has limitations, however. Plasmid transfection generally requires that cells be isolated for transfection and then implanted after transfection. Viral delivery generally requires that the appropriate receptor be located on the surface of the target cell in order to facilitate viral entry into the cell.

There is tremendous potential for the use of osteoinductive proteins and peptides, particularly for the use of those proteins and peptides that act via an intracellular mechanism. What is needed is a method of delivery of effective intracellular osteoinductive proteins and peptides into cells.

SUMMARY OF THE INVENTION

The present invention provides a method of producing a cell-permeable osteoinductive polypeptide comprising introducing into a suitable host cell an expression construct encoding a cell-permeable polypeptide and an osteoinductive polypeptide positioned so that the osteoinductive polypeptide is expressed as part of a fusion protein with the cell-permeable polypeptide. The expression construct generally contains a promoter positioned to direct transcription of the polynucleotide sequence encoding the fusion product.

The expression construct may further comprise a purification tag. The cell-permeable polypeptide may be chosen from the group consisting of HIV-TAT, VP-22, a growth factor signal peptide sequence, Pep-1, and a *Drosophila* Antp peptide. The osteoinductive polypeptide may be chosen from the group consisting of LMP-1, LMP-3, SEQ ID NO 1, SEQ ID NO 2, SEQ ID NO 3, SEQ ID NO 4, SEQ ID NO 5, SEQ ID NO 6, SEQ ID NO 7, SEQ ID NO 8, BMP-2, BMP-4, BMP-6, BMP-7, TGF-beta 1 and Smad.

The invention provides osteoinductive polypeptides chosen from among the group consisting of SEQ ID NO 1, SEQ ID NO 2, SEQ ID NO 3, SEQ ID NO 4, SEQ ID NO 5, SEQ ID NO 6, SEQ ID NO 7, and SEQ ID NO 8, or combinations thereof.

The invention also provides a method of inducing bone formation in a mammal comprising administering an effective amount of a fusion polypeptide comprising a protein transduction domain and at least one osteoinductive polypeptide. The fusion polypeptide may be administered as an implant and may be administered to at least one multipotent progenitor cell, which can be implanted into a mammal to promote osteoinduction.

The invention also provides a polynucleotide encoding a fusion protein comprising a protein transduction domain and at least one osteoinductive polypeptide, the protein transduction domain being chosen from among a variety of protein transduction, membrane-translocation, and other similar polypeptides represented, for example, by HIV-TAT, VP-22, a growth factor signal peptide sequence, Pep-1, and a *Drosophila* Antp peptide. The osteoinductive polypeptide may be chosen from the group consisting of LMP-1, LMP-3, SEQ ID NO 1, SEQ ID NO 2, SEQ ID NO 3, SEQ ID NO 4, SEQ ID NO 5, SEQ ID NO 6, SEQ ID NO 7, SEQ ID NO 8, BMP-2, BMP-4, BMP-6, BMP-7, TGF-beta 1 and Smad.

A method of inducing proteoglycan synthesis in a mammal is also provided. The method comprises administering an effective amount of a fusion polypeptide comprising a protein transduction domain and at least one osteoinductive polypeptide. The fusion polypeptide may be administered as an implant, and may be administered to at least one multipotent progenitor cell.

An isolated fusion polypeptide comprising a membrane-translocating peptide operably linked to an osteoinductive polypeptide is provided by the invention. The membrane-translocating peptide may be chosen from the group consisting of HIV-TAT, VP-22, a growth factor signal peptide sequence, Pep-1, and a *Drosophila* Antp peptide and the osteoinductive polypeptide may be chosen from the group consisting of LMP-1, LMP-3, SEQ ID NO 1, SEQ ID NO 2, SEQ ID NO 3, SEQ ID NO 4, SEQ ID NO 5, SEQ ID NO 6, SEQ ID NO 7, SEQ ID NO 8, BMP-2, BMP-4, BMP-6, BMP-7, TGF-beta 1 and Smad.

The invention provides a method of inducing osteoblast differentiation in a progenitor cell, the method comprising administering to the progenitor cell an effective amount of a fusion polypeptide comprising a protein transduction domain and at least one osteoinductive polypeptide. The protein transduction domain can be chosen from the group represented by HIV-TAT, VP-22, a growth factor signal peptide sequence, Pep-1, and *Drosophila* Antp polypeptides and the osteoinductive polypeptide may be chosen from the group represented by LMP-1, LMP-3, SEQ ID NO 1, SEQ ID NO 2, SEQ ID NO 3, SEQ ID NO 4, SEQ ID NO 5, SEQ ID NO 6, SEQ ID NO 7, SEQ ID NO 8, BMP-2, BMP-4, BMP-6, BMP-7, TGF-beta 1 and Smad.

BRIEF DESCRIPTION OF THE DRAWINGS

FIG. 4 is a table summarizing parameters and results of LMP-1 administration via a PTD/LMP-1 fusion protein in Harlan athymic rats.

FIG. 5 is a table summarizing parameters and results of LMP-1 administration via a PTD/LMP-1 fusion protein in New Zealand White rabbits.

FIG. 6 is a table summarizing results of administration of the indicated osteoinductive peptides via a PTD/peptide fusion protein in Harlan athymic rats, and, where indicated, New Zealand White rabbits. Bone growth was detected by x-ray, and, where indicated, was also palpable.

DETAILED DESCRIPTION

Figure 1:
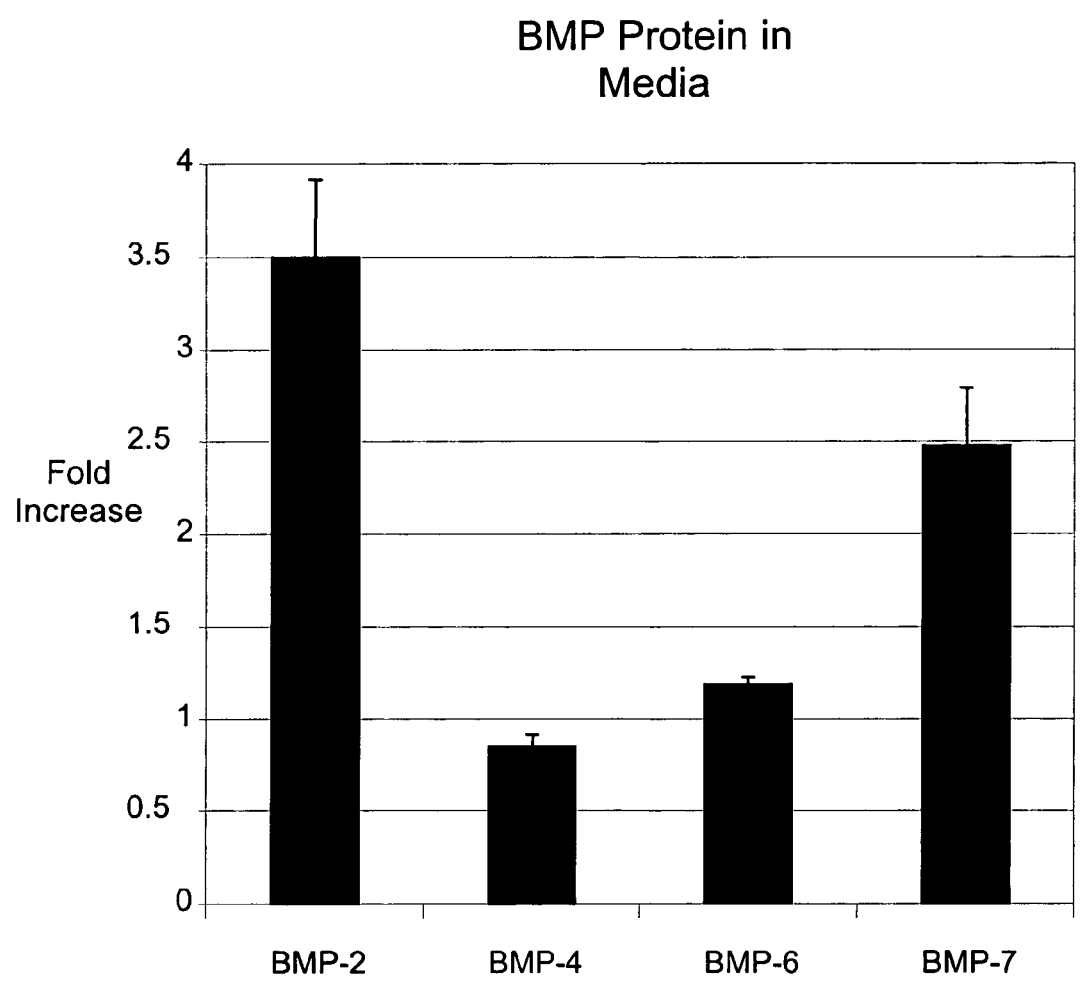
FIG. 1 is a graph of BMP protein levels in media 6 days after treatment of annulus cells with LMP-1 (AdLMP-1 at MOI 25). The protein levels of BMP-2 and BMP-7 were increased significantly but BMP-4 and BMP-6 protein levels were not significantly different from media of untreated control cells. Each result is expressed as a ratio in proportion to the value from untreated cells. The mean and SEM for seven samples are reported. (*$p<0.05$**$p<0.01$ versus NT).
Figure 2:
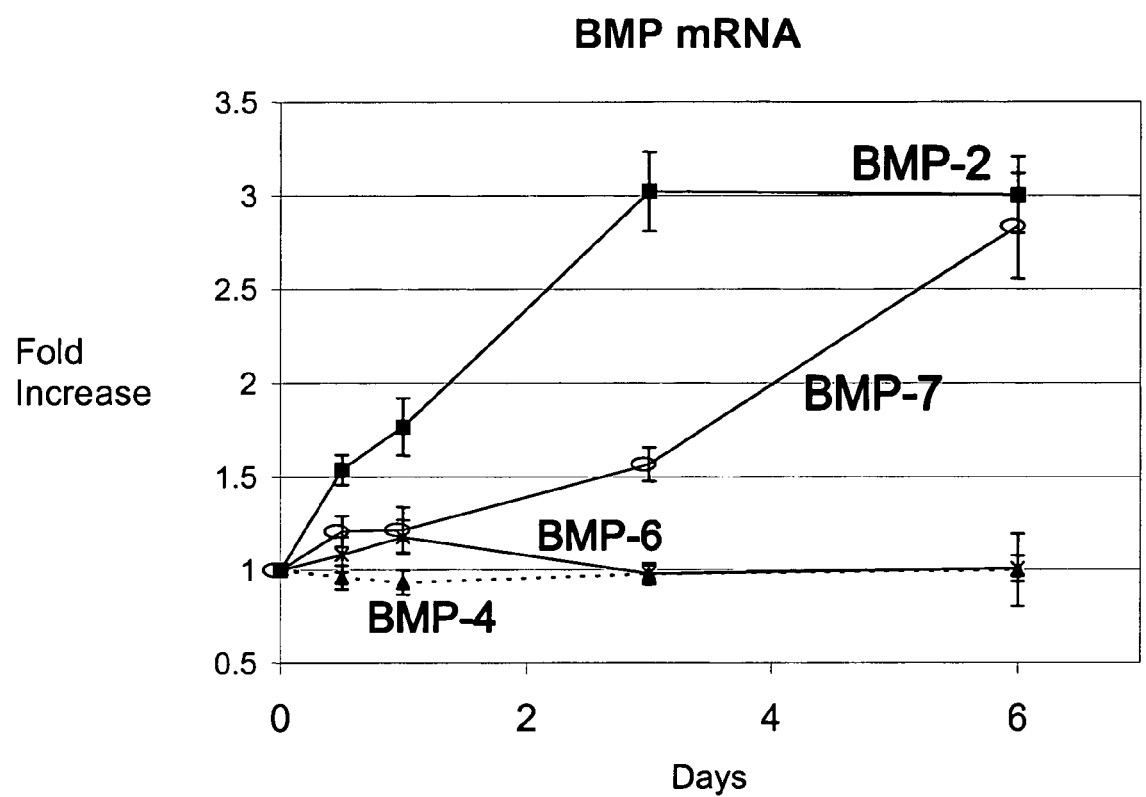
FIG. 2 illustrates time-course BMP mRNA levels after treatment of annulus cells with LMP-1 (AdLMP-1 at MOI 25). BMP-2 mRNA level was upregulated significantly as early as 12 hours after AdLMP-1 treatment and reached a plateau 3 days after AdLMP-1 treatment. BMP-7 mRNA level was significantly increased 3 days after AdLMP-1 treatment. Each result is expressed as a ratio to values from untreated cells at the same time point. The mean and SEM for six samples are reported. (**$p<0.01$ versus NT for corresponding time point).
Figure 3:
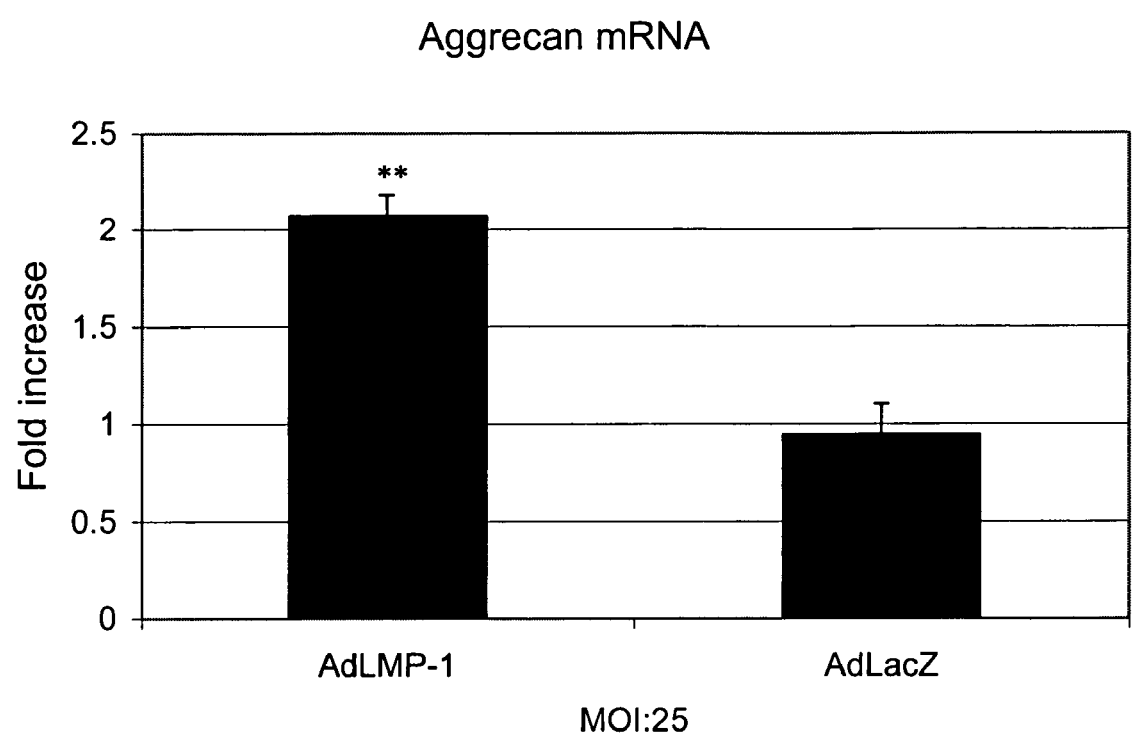
FIG. 3 graphs aggrecan mRNA level in annulus cells after treatment with LMP-1 (AdLMP-1) measured by realtime PCR. The mRNA level of aggrecan was significantly increased 6 days after treatment with AdLMP-1 at MOI 25 as compared to untreated cells. The mRNA level of aggrecan was not changed in cells treated with AdLacZ as compared to untreated cells. Each result is expressed as a ratio to values from untreated cells. The mean and SEM for nine samples are reported. AdLMP-1: MOI 25, AdLacZ: MOI 25. (**$p<0.01$ versus NT).

The inventors have discovered that a fusion protein comprising a protein transduction polypeptide and an osteoinductive polypeptide can be effectively used to promote bone development and intervertebral disc regeneration in vivo. The invention therefore provides osteoinductive polypeptides for intracellular delivery, polynucleotides encoding such osteoinductive polypeptides and protein transduction sequences, and methods of utilizing these fusion proteins to promote bone development and intervertebral disc regeneration in vivo.

Previous work has demonstrated that LIM mineralization protein splice variants 1 and 3 (LMP-1 and LMP-3) are osteoinductive, while LMP-2 does not appear to have such osteoinductive potential. A forty amino acid sequence corresponding to amino acids 94-133 of the amino acid sequence of human LMP-1 (hLMP-1) is common to both LMP-1 and LMP-3. The inventors therefore surmised that this unique region of the proteins might, in itself, have osteoinductive potential. Peptides comprising overlapping segments of this sequence were designed and used to test the inventors' hypothesis. Their results indicate that peptides derived from LMP-1 and LMP-3 have osteoinductive potential. When used in vivo, these peptides demonstrated the ability to induce bone formation. FIG. 6 indicates peptides which have demonstrated osteoinductive functionality when introduced into cells as part of the fusion protein of the present invention in the method of the present invention.

Protein transduction polypeptides facilitate the uptake and subsequent expression of nucleic acid sequences or therapeutic proteins. In the literature, they may be referred to alternately, and often interchangeably, as cell-permeable peptides, protein transduction domains, membrane transport sequences, and membrane-translocating peptides. They function to transport an attached peptide, polypeptide, or protein through the cell membrane into the interior of the cell in a receptor-independent manner. A fusion protein utilizing a protein transduction domain can comprise one or more peptides, polypeptides, or proteins operably linked to the protein transduction domain. In the present invention, such a fusion protein can comprise a protein transduction domain and at least one osteoinductive peptide, polypeptide, or protein, or combinations thereof. These peptides can be used to transduce autologous, allogeneic, or xenogeneic cells or tissues of ectodermal, mesenchymal, or hematopoetic origin and infuse or implant them into the recipient to induce or contribute to the formation of new tissue. In the method of the present invention, such polypeptides facilitate the uptake of proteins that can induce cells such as, for example, multipotent progenitor (stem) cells, to produce, for example, BMP-2, BMP-4, BMP-6, BMP-7, BMP-9, BMP-12, BMP-13, aggrecan, collagen type I, collagen type II, versican, lumican, fibromodulin, biglycan, and decorin. Effective amounts of polypeptides of the present invention are indicated in the experimental design and results disclosed herein, but may also be determined by one of skill in the art based upon the disclosure of effective amounts provided herein.

Human LIM mineralization protein-1 (hLMP-1), one of a family of LMP proteins, is an intracellular regulatory protein that can enhance the efficacy of bone mineralization in vitro and in vivo. Human LMP-1 is so named because it possesses a characteristic structural motif composed of two special zinc fingers that are joined by an amino acid spacer. LIM mineralization protein splice variants and their uses have been described by the inventors in U.S. Pat. Nos. 6,300,127; 6,444,803; and 6,521,750. The sequences of LMP-1, LMP-2, and LMP-3 have also been disclosed in those patents. On Jul. 22, 1997, a sample of 10-4/RLMP (*Rattus norvegicus* LIM mineralization protein cDNA) in a vector designated pCMV2/RLMP (which is vector pRc/CMV2 with insert 10-4 clone/RLMP) was deposited with the American Type Culture Collection (ATCC), 12301 Parklawn Drive, Rockville, Md. 20852, and was assigned accession number 209153. On Mar. 19, 1998, a sample of the vector pHis-A with insert HLPM is (*Homo sapiens* LIM mineralization protein cDNA) was deposited at the American Type Culture Collection and assigned accession number 209698.

A serotype 5 adenovirus (Ad5) has been employed for the delivery of LMPs to a variety of cells and tissues including cells derived from peripheral blood and bone marrow. (Boden, et al., "Adenoviral Delivery of LMP-1 Induces Consistent Spine Fusion", 47$^{th}$ Annual Meeting, Orthopaedic Research Society, San Francisco, Calif. (2001)). However, the Ad5 virus utilizes a specific receptor (i.e., coxsackie adenovirus receptor or CAR), which is absent, or present in limited quantities, in these cells. Protein transduction across the cell membrane to facilitate intracellular delivery of proteins without receptor-mediated mechanisms offers an attractive alternative to allow treatment of a variety of cell and tissue types.

The actions of LMPs and other osteoinductive proteins indicate that they have therapeutic potential in a variety of tissues, such as brain, spinal cord, peripheral nerve, bone, cartilage, intervertebral discs, connective tissue, tendons, and ligaments. Delivery of LMPs, for example, to a variety of tissues can be accomplished by delivery systems comprising, for example, collagen, collagen ceramic combinations, demineralized bone matrix, natural or synthetic polymers such as elastin, fibrin, polylactic acid, polyglycolic acid, polycaprolactone, polypropylene fumarate, polyvinyl alcohol, polyesters, polyethers, polyhydroxyls, and structural implants. Such matrices may be injectable, moldable, solid implants, structural implants, or combinations thereof.

The present inventors have discovered that PTDs can be used to deliver functional osteoinductive proteins into cells and to effectively induce osteogenesis and proteoglycan synthesis. Such cell-permeable peptide import (CPPI) provides a method for delivering osteoinductive proteins into a variety of cell types. An 11 amino acid peptide, initially derived from the HIV-1 TAT protein, was successfully used to deliver osteoinductive proteins into cells. The TAT peptide can be over-expressed in bacterial cells using the pTAT-HA vector. A recombinant human gene can be inserted into this vector in such a manner as to produce a fusion protein containing both the TAT peptide sequence as well as the gene product of interest. Furthermore, the PTD/osteoinductive polypeptide can be expressed in conjunction with a polyHis tag in order to facilitate isolation and purification of the fusion protein. The pTAT-HA vector and a purification protocol for TAT fusion proteins have been described previously by Nagahara, et al. (*Nature Medicine*, Vol. 4) p. 1449-1452, December 1998).

A peptide sequence as found in a variety of PTDs can facilitate entry into cells in a coxsackie-adenovirus receptor (CAR)-independent manner, thereby improving transduction efficiencies to target cells and subsequently lowering the required amounts of nucleic acid or protein needed to achieve the desired effect. PTD fusion proteins therefore provide a therapeutic tool that may be used to reduce the cost of therapy.

In one embodiment of the invention, a fusion protein of a protein transduction domain and an osteoinductive protein is provided. Osteoinductive proteins include, but are not limited to, LIM mineralization proteins (LMPs), bone morphogenetic proteins (BMP) and Smad proteins. As used herein, "osteoinductive proteins," "osteoinductive polypeptides," and "osteoinductive peptides" may be used interchangeably to refer to either a peptide or polypeptide of varying length or a full-length protein with osteoinductive functionality.

A fusion protein comprising a PTD and a LIM mineralization protein is provided as one embodiment of the invention. The fusion protein can comprise a PTD and one or more LIM mineralization proteins or polypeptides. Useful LIM mineralization proteins include, for example, LMPs as disclosed in U.S. Pat. Nos. 6,300,127; 6,444,803; and 6,521,750; as well as pending U.S. patent application Ser. No. 09/959,578, filed Apr. 28, 2000. Preferably, the LMP is RLMP, HLMP-1, HLMP-1s, HLMP-2, HLMP-3, or a peptide derived therefrom. These peptides can include, for example, SEQ ID NO 1, SEQ ID NO 2, SEQ ID NO 3, SEQ ID NO 4, SEQ ID NO 5, SEQ ID NO 6, SEQ ID NO 7, or a polypeptide as in SEQ ID NO 8.

The nucleotide sequence encoding the LIM mineralization protein preferably hybridizes under standard conditions to a nucleic acid molecule complementary to the full length of the following sequence:

tcctcatccg ggtcttgcat gaactcggtg (SEQ. ID. NO. 9)

or hybridizes under highly stringent conditions to a nucleic acid molecule complementary to the full length of the following sequence:

gcccccgccc gctgacagcg ccccgcaa (SEQ. ID. NO. 10), or both.

"Standard hybridization conditions" will vary with the size of the probe, the background and the concentration of the nucleic acid reagents, as well as the type of hybridization (in situ, Southern blot, or hybridization of DNA-RNA hybrids (Northern blot)). The determination of "standard hybridization conditions" is within the level of skill in the art. Methods include, for example, those described in U.S. Pat. No. 5,580,775 (Fremeau, et al.), Southern, *J. Mol. Biol.*, 98:503 (1975), Alwine, et al., *Meth. Enzymol.*, 68:220 (1979), and Sambrook, et al., *Molecular Cloning: A Laboratory Manual*, 2nd edition, Cold Spring Harbor Press, 7.19-7.50 (1989).

One set of standard hybridization conditions involves pre-hybridizing a blot at 42° C. for 2 hours in 50% formamide, 5×SSPE (150 nM NaCl, 10 mM NaH$_2$PO$_4$ [pH 7.4], 1 mM EDTA [pH 8.0]) 5×Denhardt's solution (20 mg Ficoll, 20 mg polyvinylpyrrolidone and 20 mg BSA per 100 ml water), 10% dextran sulphate, 1% SDS and 100 µg/ml salmon sperm DNA. A $^{32}$P-labeled cDNA probe is added, and further hybridizing continued for 14 hours. Afterward, the blot is washed twice with 2×SSPE, 0.1% SDS for 20 minutes at 22° C., followed by a 1 hour wash at 65° C. in 0.1×SSPE, 0.1% SDS. The blot is then dried and exposed to x-ray film for 5 days in the presence of an intensifying screen.

Under "highly stringent conditions", a probe will hybridize to its target sequence if those two sequences are substantially identical. Techniques are known to those of skill in the art for determining the conditions under which only substantially identical sequences will hybridize while non-identical sequences will not.

As used herein, the term "protein" is intended to include mimetics and the term "amino acid" is intended to include L-form, D-form, and modified amino acids. These substitutions may be made by one of skill in the art, using the known structural similarities between the molecules. The amino acid sequence is also intended to include any peptide or protein sequence that may include additional amino acids either N-terminal or C-terminal to the listed sequence, or both. The term "osteoinductive protein" is intended to include variants or biologically active fragments of the polypeptide, as well as full-length proteins.

It is well known in the art that a single amino acid may be encoded by more than one nucleotide codon, and that the nucleotide sequence may be modified to produce an alternate nucleotide sequence that encodes the same peptide. Therefore, alternate embodiments of the present invention include alternate DNA sequences encoding peptides containing the amino acid sequences as previously described. DNA sequences encoding peptides containing the claimed amino acid sequence include DNA sequences which encode any combination of the claimed sequence and other amino acids located N-terminal or C-terminal to the claimed amino acid sequence. It is to be understood that amino acid and nucleic acid sequences may include additional residues, particularly N- or C-terminal amino acids or 5' or 3' nucleotide sequences, and still be essentially as set forth in the sequences disclosed herein, as long as the sequence confers osteoinductive potential upon the expressed polypeptide or protein.

Additional nucleic acid bases may be added either 5' or 3' to the nucleotide sequence encoding the osteoinductive polypeptide, and may be combined with other DNA sequences, such as promoters, polyadenylation signals, additional restriction enzyme sites, multiple cloning sites, other coding segments, and the like. Therefore, overall length of such a polynucleotide may vary considerably.

It is to be understood that a "variant" of a polypeptide is not completely identical to the native protein. A variant of an osteoinductive polypeptide or protein, for example, can be obtained by altering the amino acid sequence by insertion, deletion or substitution of one or more amino acids. The amino acid sequence of the polypeptide or protein can be modified, for example, by substitution to create a polypeptide having substantially the same or improved qualities as compared to the native polypeptide. The substitution may be a conserved substitution. A "conserved substitution" is a substitution of an amino acid with another amino acid having a side chain that is similar in polar/nonpolar nature, charge, or size. The 20 essential amino acids can be grouped as those having nonpolar side chains (alanine, valine, leucine, isoleucine, proline, phenylalanine, and tryptophan), uncharged polar side chains (methionine, glycine, serine, threonine, cystine, tyrosine, asparagine and glutamine), acidic side chains (aspartate and glutamate), and basic side chains (lysine, arginine, and histidine). Conserved substitutions might include, for example, Asp to Glu, Asn, or Gln; His to Lys, Arg or Phe; Asn to Gln, Asp or Glu; and Ser to Cys, Thr or Gly. Alanine, for example, is often used to make conserved substitutions.

To those of skill in the art, variant polypeptides can be obtained by substituting a first amino acid for a second amino acid at one or more positions in the polypeptide structure in order to affect biological activity. Amino acid substitutions may, for example, induce conformational changes in a polypeptide that result in increased biological activity.

Those of skill in the art may also make substitutions in the amino acid sequence based on the hydrophilicity index or hydropathic index of the amino acids. A variant amino acid molecule of the present invention, therefore, has less than one hundred percent, but at least about fifty percent, and preferably at least about eighty to about ninety percent amino acid sequence homology or identity to the amino acid sequence of a polypeptide comprising the amino acid sequence of LMP-1, LMP-2, LMP-3, SEQ ID NO 1, SEQ ID NO 2, SEQ ID NO 3, SEQ ID NO 4, SEQ ID NO 5, SEQ ID NO 6, SEQ ID NO 7, or a polypeptide as in SEQ ID NO 8. Therefore, the amino acid sequence of the variant osteoinductive polypeptide or protein corresponds essentially to the native osteoinductive polypeptide or protein amino acid sequence. As used herein, "corresponds essentially to" refers to a polypeptide sequence that will elicit a similar biological and enzymatic activity to that generated by an osteoinductive polypeptide or protein comprising LMP-1, LMP-2, LMP-3, SEQ ID NO 1, SEQ ID NO 2, SEQ ID NO 3, SEQ ID NO 4, SEQ ID NO 5, SEQ ID NO 6, SEQ ID NO 7, or a polypeptide as in SEQ ID NO 8, such activity being at least about 70 percent that of the native osteoinductive protein, and more preferably greater than 100 percent of the activity of the native osteoinductive protein.

A variant of the osteoinductive protein may include amino acid residues not present in a corresponding osteoinductive protein comprising LMP-1, LMP-2, LMP-3, SEQ ID NO 1, SEQ ID NO 2, SEQ ID NO 3, SEQ ID NO 4, SEQ ID NO 5, SEQ ID NO 6, SEQ ID NO 7, or SEQ ID NO 8, or may include deletions relative to the osteoinductive protein comprising LMP-1, LMP-2, LMP-3, SEQ ID NO 1, SEQ ID NO 2, SEQ ID NO 3, SEQ ID NO 4, SEQ ID NO 5, SEQ ID NO 6, SEQ ID NO 7, or SEQ ID NO 8. A variant may also be a truncated "fragment," as compared to the corresponding protein comprising LMP-1, LMP-2, LMP-3, SEQ ID NO 1, SEQ ID NO 2, SEQ ID NO 3, SEQ ID NO 4, SEQ ID NO 5, SEQ ID NO 6, SEQ ID NO 7, or SEQ ID NO 8, the fragment being only a portion of the full-length protein or polypeptide.

Bone morphogenetic proteins (BMPs) are members of the TGF-β superfamily of proteins. BMPs have been shown to induce ectopic bone or cartilage formation. According to the invention, a fusion protein of a PTD and a bone morphogenetic protein is also provided. BMPs include, for example, BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, GDF-1, GDF-3, GDF-8 and GDF-9. Bone morphogenetic proteins BMP-2, BMP-4, BMP-5, BMP-6, BMP-7, BMP-8, or BMP-9 can be especially useful in the method of the present invention.

Smad proteins are intracellular proteins that mediate signaling from receptors for extracellular TGF-beta-related factors (Heldin. et al., "TGF-β Signalling from Cell Membrane to Nucleus through SMAD Proteins", *Nature*, Vol. 390 (1997)). Smad proteins can be activated (i.e., phosphorylated) by the binding of a BMP to its receptor. Upon activation, the Smad proteins translocate to the nucleus where they regulate gene expression. A fusion protein of a PTD and a Smad protein is also provided in the present invention. Smad-1, Smad-2, Smad-3, Smad-4, Smad-5, Smad-6, Smad-7 or Smad-8 can be especially useful for promoting osteoinduction when delivered as a fusion protein with a protein transduction domain as in the present invention.

The protein transduction domain according to the invention can be any peptide, mimetic, or peptide nucleic acid (PNA) sequence that can traverse the plasma membrane of a cell to deliver an attached or accompanying protein, peptide, or nucleic acid to the interior of the cell. The inventors have demonstrated that osteoinductive proteins can be delivered intracellularly (as a fusion protein moiety, for example) without impairing their ability to promote osteoinduction and proteoglycan synthesis. PTDs include, for example, polypeptides derived from the *Drosophila* homeotic transcription factor Antennapedia (Antp), the herpes simplex virus (HSV) protein VP22, signal peptide sequences from growth factors such as Kaposi's fibroblast growth factor (K-FGF) (Lin, et al., *J. Biol. Chem.*, Vol. 270, p. 14255-14258, 1995) a membrane translocation sequence derived from the K-FGF signal peptide sequence (Rojas, et al, *Nat. Biotech.*, Vol. 16, p. 370-375, 1998), and the human immunodeficiency virus (HIV)-1 transcriptional activator TAT (Fawell, et al., *Proc. Natl. Acad. Sci.*

*USA*, Vol. 91, p. 664-668, 1994). PTDs are disclosed in U.S. Pat. No. 5,652,122, and in Schwarze. et al., "Protein Transduction: Unrestricted Delivery into all Cells", *Trends in Cell Biology*, Vol. 10 (2000). The inventors have found the HIV-TAT PTD to be especially useful in the present invention.

A nucleic acid comprising a nucleotide sequence encoding a fusion protein operably linked to a promoter, wherein the fusion protein comprises a protein transduction domain (PTD) and an osteoinductive protein, is also provided. The nucleic acid can be part of a vector (e.g., an expression vector such as a plasmid). Osteoinductive proteins can include, for example, LIM mineralization proteins, bone morphogenetic proteins, Smad proteins, and osteoinductive peptides and polypeptides derived therefrom. Examples of osteoinductive peptides and polypeptides include SEQ ID NO 1, SEQ ID NO 2, SEQ ID NO 3, SEQ ID NO 4, SEQ ID NO 5, SEQ ID NO 6, SEQ ID NO 7, and SEQ ID NO 8.

Methods of delivering osteoinductive proteins into cells are also provided by the present invention. In a method of the invention, at least one osteoinductive protein can be delivered into a cell via transduction wherein a fusion protein comprising a protein transduction domain (PTD) and an osteoinductive protein is contacted with the cell so that the fusion protein is delivered into the cell, the delivery being facilitated by the protein transduction domain or cell-permeable peptide The cells into which the osteoinductive proteins can be delivered include, for example, osseous (i.e., bone forming) and non-osseous cells. Such cells may include, for example, buffy coat cells, stem cells (e.g., mesenchymal stem cells, multipotent and pluripotent stem cells), intervertebral disc cells (e.g., cells of the annulus fibrosus and cells of the nucleus pulposus), mesenchymal cells, hematopoietic cells, endothelial cells and muscle cells. Stem cells can be derived from autalogous or allogeneic tissue.

Cells transduced with or expressing a fusion protein of a protein transduction domain (PTD) and an osteoinductive protein are also provided. Such cells may include, but are not limited to, buffy coat cells, stem cells (e.g., mesenchymal stem cells and pluripotential stem cells), intervertebral disc cells (e.g., cells of the annulus fibrosus and cells of the nucleus pulposus), mesenchymal cells, hematopoietic cells, endothelial cells and muscle cells. Cells containing a fusion protein of a PTD and an osteoinductive protein as described herein can be implanted into the body of a mammal to induce bone formation. Methods of inducing bone formation using LMPs as osteoinductive proteins are described, for example, in U.S. Pat. No. 6,300,127. Cells comprising a fusion protein of a PTD and an osteoinductive protein may also be implanted into the intervertebral disc, for example, to stimulate proteoglycan and/or collagen synthesis as set forth in U.S. patent application Ser. No. 10/292,951, filed Nov. 13, 2002, pending.

A Conjugate of a PTD and a nucleic acid comprising a nucleotide sequence encoding an osteoinductive protein is also provided. The PTD/nucleic acid conjugate can be used to direct over-expression of an osteoinductive protein to promote bone formation or disc regeneration, for example. Osteoinductive proteins encoded by the nucleotide sequence can include, but are not limited to, LMPs, BMPs, and Smad proteins. Methods for chemically linking peptides to nucleic acids are known in the art. One such method is described in U.S. Pat. No. 5,652,122. The nucleic acid can be in the form of an expression vector comprising a nucleotide sequence encoding an osteoinductive protein operably linked to a promoter.

Methods of the present invention can be used to induce the expression of one or more bone morphogenetic proteins or transforming growth factor-β proteins in a cell as described in copending U.S. patent application Ser. No. 10/382,844, filed Mar. 7, 2003. For example, the expression of one or more proteins selected from the group consisting of BMP-2, BMP-4, BMP-6, BMP-7, TGF-β1 and combinations thereof can be induced by contacting a cell with a fusion protein comprising a PTD and an osteoinductive protein according to the invention. Additionally, cells which over-express one or more proteins selected from the group consisting of BMP-2, BMP4, BMP-6, BMP-7, TGF-β1 and combinations thereof are also provided according to the invention. The cell can be any somatic cell including, but not limited to, a stem cell, a buffy coat cell, a bone marrow cell, a peripheral blood cell or a fat cell. The cell can be a stem cell derived from autologous or allogeneic tissue.

Stem cells, or multipotent progenitor cells, can provide a source of cells from which to generate osteoblasts. These cells may be isolated at various stages of differentiation and induced to differentiate in specific lineage pathways. The cells may be used to treat bone diseases such as osteoporosis or osteogenesis imperfecta, as well as non-healing fractures. Core binding factor alpha 1 (Cbfa1) has been demonstrated to be necessary for osteogenesis. BMP-2, BMP-4, and BMP-7, which are known to induce osteoblast differentiation, up-regulate Cbfa1 expression. BMP-8 and Smad-3 are up-regulated during osteoblast differentiation. Activation of TGF-beta/BMP-Smad signaling has been shown to promote Cbfa1 expression, and osteoblast differentiation. The present invention provides fusion proteins comprising functional BMPs, LMPs, Smad proteins, or a combination thereof, for example, to promote osteoblast differentiation in cells such as human bone marrow-derived mesodermal progenitor cells. Suitable cells may include, for example, multipotent cells such as those described by Jiang, et al. (*Nature*, Vol. 418, p. 41-49, 2002). Administration of suitable osteoinductive proteins or polypeptides, or combinations thereof, can be performed ex vivo before implantation of the cells, or in vivo following implantation or injection. For in vivo administration, osteoinductive proteins of the present invention can be injected at a target site so that they can be delivered to the interior of nearby cells via a PTD or cell-permeable peptide, for example. Alternately, an implant comprising a carrier in combination with a PTD/osteoinductive polypeptide may be used. Implants may contain reservoirs in which to place the PTD/osteoinductive polypeptide for release into the surrounding tissue, or may comprise a porous composition that has been soaked in a solution containing one or more PTD/osteoinductive polypeptide constructs. Hydrogels, time-release capsules or spheres, liposomes, microspheres, nanospheres, biodegradable polymers, or other such drug delivery systems may also be employed to deliver peptides and proteins of the present invention to target cells and tissues. U.S. Pat. No. 6,475,516 (DiCosmo, et al.), for example, provides hydrogels loaded with liposomal therapeutic agents such as antibiotics, the hydrogels being covalently bonded to the surface of an in-dwelling medical device such as an implant.

A hallmark of disc degeneration is the decreased production of proteoglycans in the disc, especially sulfated-glycosaminoglycans (sGAG) and aggrecan. A decrease in the production rate of aggrecan, the major proteoglycan of the intervertebral disc, is an important factor in intervertebral disc degeneration. Because of the central role of proteoglycans in the function of the intervertebral disc, restoration of normal proteoglycan production of the intervertebral disc may be critically important in any biological treatment of intervertebral disc degeneration.

The inventors performed experiments which demonstrated that LMP-1 over-expression or intracellular administration increases disc cell proteoglycan production in vitro and in vivo. LMP-1 over-expression induces the upregulation of BMP-2 and BMP-7 mRNA in vitro and in vivo. Noggin, which specifically inhibits these BMP-2 and BMP-7, inhibits proteoglycan upregulation by AdLMP-1, indicating that LMP-1 induced upregulation of proteoglycan is mediated by the upregulation of BMPs. LMP-1 administration via gene therapy or protein therapy (e.g., delivery by PTD conjugates) therefore can be used to stimulate proteoglycan production in discs and play a therapeutic role in disc regeneration.

Cytokines such as TGF-β1, IGF-1, and EGF have been shown to stimulate intervertebral disc cell mitosis and, to some extent, proteoglycan production. Other cytokines such as BMP-2 and BMP-7 have also been shown to be effective in stimulating proteoglycan production. Because cytokines are small water soluble molecules, however, they rapidly diffuse away from the intervertebral disc or become inactivated by other regulatory factors. LIM Mineralization Protein-1 (LMP-1) is an intracellular regulatory molecule that is known to induce the secretion of multiple different BMPs from leukocytes and osteoblasts. By delivering LMP-1, LMP-2, LMP-3, or an osteoinductive peptide derived from LMP-1 or LMP-3, or a combination thereof, into the cell, particularly via a PTD/nucleic acid conjugate, BMP production can be stimulated from within the cells. Suitable osteoinductive peptides include, for example, SEQ ID NO 1, SEQ ID NO 2, SEQ ID NO 3, SEQ ID NO 4, SEQ ID NO 5, SEQ ID NO 6, SEQ ID NO 7, or a polypeptide as in SEQ ID NO 8.

The present invention may be more fully understood by reference to the following non-limiting examples.

EXAMPLES

The synthesis and use of a (His)6 TAT-LMP protein conjugate, comprising the protein transduction domain of HIV-Tat and the LMP-1 protein, is described below. The pTAT-HA-vector was obtained under a material transfer agreement from Washington University (St. Louis, Mo.).

An NcoI restriction site was added to the 5' end of hLMP-1 by utilizing 10 pcDNA3.1/hLMP-i as the template for PCR with the following primers:

Fwd: 5'-CCATGGATTCCTTCAAAGTAGTGC-3' (SEQ. ID. NO. 11)

Rev: 5'-CAGGGCGGGCGGCTGGTAG-3' (SEQ. ID. NO. 12)

The reaction was performed at: 95° C. for 2 Min. [95° C., 30 sec; 66° C., 30 sec; 72° C., 1 mm]×25, and 72° C. 10 mm. The PCR product was cloned into PCRII-TOPO vector (Invitrogen) and appropriate clones were identified by sequencing.

Construction of the (His)6 TAT-LMP vector was accomplished by restriction endonuclease digestion of plasmid clones with NcoI and ClaI, and purification of the resulting product by agarose gel electrophoresis and electroelution. The full-length hLMP-1 sequence was isolated by restriction digest of the pcDNA3.1/hLMP-1 vector with ClaI and EcoRI, and purification of the resulting product by agarose gel electrophoresis and electroelution. The pTAT-HA-vector was also subjected to restriction digestion with NcoI and EcoRI, and the resulting linearized vector was purified by agarose gel electrophoresis and electroelution. Products were then ligated by standard procedures overnight at 16° C. Correctly ligated products (5' hLMP-1+3' hLMP-1+linearized pTAT-HA-vector=(His)6 TAT-LMP vector) were determined by subsequent agarose gel electrophoreses and molecular weight determinations.

Ligation products were transfected into BL21 (DE3) competent cells and suitable clones were identified by restriction analysis.

Synthesizing and Harvesting the $(His)_6$ TAT-LMP Protein

Appropriate BL21 (DE3) *Eschericia coli*-colonies containing positive clones of $(His)_6$ TAT-LMP fusion constructs were grown to 0.8 OD (600 nm) and protein production was induced with 100 μM IPTG for 4 h at 37° C. Induced cells were harvested by standard methods and lysed (20 mM $PO_4$ buffer, pH 7.2, 8 M urea, 100 mM NaCl, 20 mM Imidazole) by sonication (4×20 s, each with 2 mm rest periods, 4° C.).

The lysate was clarified by centrifugation (10000×g) and the resulting supernatant applied to a $Ni^{2+}$ sepharose affinity column (Invitrogen) under gravity flow conditions. The column was washed (20 mM $PO_4$ buffer, pH 6.0, 8 M Urea, 250 mM NaCl, 20 mM Imidazole) and then bound proteins eluted (20 mM $PO_4$ buffer, pH 4.0, 8 M Urea, 500 mM NaCl).

Eluate was subjected to anion exchange chromatography (Hitrap Q HP, 5 mL, Pharmacia) using a linear gradient (Buffer A: 20 mM sodium carbonate, pH 11, 8 M Urea; Buffer B: 20 mM sodium carbonate, pH 11, 8 M Urea, 2 M NaCl) from 0% Buffer B to 100% Buffer B (40 mm @ 5 mL/min). Eluted fractions (5 mL) were analyzed for the presence of hLMP-1 by SDS-PAGE and Western blot analyses.

Fractions positive for hLMP-1 were subjected to hydrophobic interaction chromatography (Hitrap® Phenyl-sepharose, 5 mL, Pharmacia). Elution (Buffer A: 20 mM sodium carbonate, pH 10.5, 1.5 M ammonium sulfate; Buffer B: 20 mM sodium carbonate, pH 10.5) was performed with a linear gradient of 0% to 100% Buffer B for 20 mm @ 5 mL/mm. Eluted fractions (5 mL) were analyzed for the presence of hLMP-1 by SDS-PAGE and Western blot analyses. Fractions positive for $(His)_6$ TAT-LMP fusion protein were lyophilized until used.

Use of $(His)_6$ TAT-LMP Fusion Protein for De Novo Bone Formation

Lyophilized fractions (55 pg) were resuspended into 40 mM KOH to (Stock Solution; 1.0 μM). Human buffy coat cells were prepared as described in Viggeswarapu, et al., *J. Bone Joint Surg.*, Vol. 83(3), p. 364 (2001). These cells were mixed with 5 μL of $(His)_6$ TAT-LMP fusion protein in alpha MEM (Gibco) and incubated for 30 min.@ 37° C.

An appropriate volume of human buffy coat cells containing the $(His)_6$ TAT-LMP fusion protein was then applied to a porous collagen matrix for implantation. To demonstrate de novo bone formation in vivo, 100 μL of cell suspension was applied via sterile pipette to a sterile 5×5 mm type I human collagen disc for implantation into rats. A similar quantity of cell suspension was applied to 10×25 mm sheets for implantation to promote spine fusion. Discs were surgically implanted subcutaneously in the chest/abdomen of 4-5 week old athymic rats (rnu⁻/rnu⁻). The animals were sacrificed at 4 weeks, at which time discs were excised, fixed in 70% ethanol, and analyzed by radiography and undecalcified histologic examination (sectioned to 5 μm and stained with Goldner Trichrome).

In rabbits, posterolateral lumbar spine arthrodesis was performed and carrier matrix was implanted (i.e., collagen sponge with 15% hydroxyapatite/85% tricalcium phosphate) with each side of the spine receiving $4×10^6$ transduced buffy coat cells. After 4 weeks, rabbits were euthanized and their lumbar spines excised. The status of the spine fusion was assessed by blinded manual palpation of the motion segments to detect residual motion (indicative of failed fusion), radiographs, CT scans, and non-decalcified histology.

In both rats and rabbits, radiography revealed a high level of mineralized bone formation conforming to the form of the original collagen discs or sheets containing LMP-1 transfected human buffy coat cells. No mineralized bone formation was observed in the control, and the original collagen discs or sheets appeared to be undergoing absorption. Histology revealed new bone trabeculae lined with osteoblasts in the LMP-1 transduced implants, whereas no bone was seen, and the carrier was partially resorbed, in the controls.

Use of Osteoinductive Peptides to Induce In Vivo Bone Formation

Protocols were essentially as described above. Peptides were applied to 4 separate implants (3 for rabbit), 250 microliters per disc, 6M/ml. Implants comprised collagen discs. Implants were placed within the chest of Harlan athymic rats or New Zealand White rabbits. Dose ranges tested were 5 nM, 10 nM, 12.5 nM, 15 nM, 17.5 nM, 20 nM, 22.5 nM, and 25 nM. Results are shown in FIG. 6.

LMP-1 Stimulation of sGAG Synthesis

In vitro experiments with lumbar intervertebral disc cells from Sprague-Dawley rats were performed by treating the cells with an adenovirus containing an LMP-1 nucleotide sequence insert (AdLMP-1) at various doses (multiplicity of infection 0, 5, 10, 25, 50) and culturing them for 6 days in monolayer to determine the effect of LMP-1 over-expression in vitro. The DMMB method was used to quantitate sulfated glycosaminoglycan (sGAG) level in the media. Real-time PCR was used to quantitate mRNA levels of aggrecan, over-expressed LMP-1, BMP-2, 4, 6, and 7. A direct ELISA method was used to quantiate the levels of BMP-2, 4, 6, and 7 in the media. To demonstrate that LMP-1 upregulation of disc cell proteoglycan production involves BMPs, a molecule (noggin) which specifically blocks BMP-2, 4, 6, and 7 activities was added to AdLMP-1 treated cells at different concentrations.

In vivo gene therapy experiments were performed in New Zealand White rabbits. Lumbar discs were injected with either AdLMP-1 (experimental) or an adenovirus carrying a marker gene (AdLacZ—control) at three different doses ($10^6$, $10^7$, and $10^8$ pfu/disc). Three weeks later the injected discs were harvested and the mRNA level of total LMP-1 (endogenous), over-expressed LMP-1, aggrecan, BMP-2, and BMP-7 were measured.

AdLMP-1 at a multiplicity of infection (MOI) of 25 was sufficient to induce the maximal level of sGAG upregulation. A period of 6 days in monolayer culture was required to reach the maximal level of sGAG upregulation after AdLMP-1 treatment (MOI 25). Aggrecan mRNA increased by 2 times compared to control. When the cells were cultured in alginate, the effect of AdLMP-1 treatment on sGAG production was sustained for 3 weeks. Six days after AdLMP-1 treatment, BMP-2 and BMP-7 mRNA levels increased significantly to 3.0±0.2 and 2.8±0.3 times that of controls ($p<0.01$), respectively. BMP-4 and BMP-6 mRNA levels were unchanged. BMP-2 and BMP-7 protein levels in the media were increased significantly ($p<0.01$) compared to control. In contrast, BMP-4 and BMP-6 protein levels were not elevated. Noggin at 3200 ng/ml completely blocked the upregulation of proteoglycan by AdLMP-1. Endogenous levels of LMP-1 mRNA were detected in lumbar nucleus pulposus. In vivo discs injected with $10^7$ pfu/disc of AdLMP-1 had a significantly elevated level of LMP-1, BMP-2, and BMP-7 mRNA levels compared to control.

In vitro experiments were carried out with Sprague-Dawley (SD) rat lumbar disc cells. Two tailed student t-tests were used to compare the experimental group to control group. The error bars in the figures present 1 SEM.

A replication deficient type 5 adenovirus carrying the cDNA for the human LMP-1 gene was used (AdLMP-1). Monolayer culture experiments with SD annulus cells were carried out to determine the relationship between virus dose and over-expressed LMP-1 mRNA expression using realtime PCR method using a primer that is specific for only the virally delivered LMP-1 cDNA. Monolayer culture experiments with SD annulus cells were performed to determine the relationship between virus dose and sGAG production. The sGAG levels were measured with a DMMB method. The optimal dose of AdLMP-1 was defined as the lowest dose which led to the plateau level of sGAG production. Using the optimal dose (25 MOI), a time-course experiment (9 days) was carried out to determine the minimal length of time (6 days) necessary to reach the plateau level of sGAG production The aggrecan mRNA level of AdLMP-1 treated annulus cells were compared to controls using the optimal viral dose and time determined above (AdLMP-1 at 25 MOI and six days after treatment). In order to ascertain that nucleus cells responded in a similar fashion to annulus cells, the effect of AdLMP-1 on sGAG production and cell number was determined for both annulus and nucleus cells at 25 MOI six days after treatment. To investigate the more long-term effects of AdLMP-1 treatment, sGAG accumulation in the alginate of SD annulus cells cultured in alginate was determined at 1, 2, and 3 weeks. All experiments were repeated at least twice.

Monolayer culture experiments with SD annulus cells were performed using AdLMP-1 at MOI 25. Briefly, the mRNA levels of LMP-1, BMP-2, BMP-4, BMP-6, and BMP-7 were measured with real-time PCR analysis at 0.5, 1, 3, and 6 days after AdLMP-1 treatment. Levels of BMP-2, BMP-4, BMP-6, and BMP-7 were measured in the media six days after treatment using a direct ELISA method. To determine the effect of blocking BMP activity, noggin was added to the culture media at the start of AdLMP-1 treatment. The change in sGAG level with or without noggin at various concentrations after treatment with AdLMP-1 was determined in a six day experiment To determine the in vivo effects of administration of LMP-1 (via. AdLMP-1) on aggrecan, BMP-2, and BMP-7, four New Zealand White (NZW) rabbits (3-4 kg) were used. The anterior lumbar discs L2/3, L3/4, L4/5, and L5/6 were exposed through a left retroperitoneal approach. Either the experimental virus (AdLMP-1) or control virus (AdGFP—type 5 adenovirus with Green Fluorescence Protein cDNA as insert) at $10^7$ plaque-forming units (pfu) was injected into each of the exposed disc nucleus in alternating fashion (i.e., two discs injected with AdLMP-1 and two discs injected with AdGFP in each rabbit). The virus was administered by delivery in 10 microliters of phosphate buffered saline through a 30 G Hamilton syringe. After 3 weeks, nucleus pulposus tissue from the injected lumbar discs was harvested. Nucleus tissues from two rabbits were pooled into either control or experimental disc groups to obtain sufficient mRNA for further analysis. Reverse transcription and real-time PCR were used to quantitate the mRNA levels of total LMP-1, BMP-7, and aggrecan. The primers for total LMP-1 were designed to identify both endogenous and over-expressed LMP-1.

In a second in vivo demonstration, various doses of the AdLMP-1 virus were used to establish a dose response relationship. AdLMP-1 at three different doses ($10^6$, $10^7$, $10^8$ pfu) and AdGFP at a single dose ($10^7$ pfu) were administered. In this experiment, all the discs from each animal were injected with a single dose of virus instead of alternating virus type as in the previous experiment. Eight NZW rabbits (3-4 kg) were used, two rabbits for each of the four virus groups. The rabbits were euthanized three weeks later and the nucleus pulposus was harvested. The harvested tissue from within each treatment group was pooled, mRNA isolated and used to generate corresponding cDNA. Real-time PCR was used to quantitate the mRNA levels of total LMP-1, over-expressed LMP-1, BMP-2, BMP-7, and aggrecan.

The relative amounts of over-expressed LMP-1 mRNA at 12 hours after virus treatment at different doses (MOI 0, 10, 25, and 50) were normalized to the lowest detectable level of over-expressed LMP-1 mRNA (AdLMP-1 MOI 5). Increasing the dose of AdLMP-1 resulted in statistically significant increases in over-expressed LMP-1 mRNA as compared to MOI 5. No detectable levels of over-expressed LMP-1 mRNA could be found in the untreated control or the AdLacZ control groups, indicating that AdLMP-1 induced over-expression of LMP-1 in annulus cells in a dose dependent manner.

The sGAG concentration in the culture media from annulus cells was determined 6 days after treatment with AdLMP-1 at different doses. The sGAG concentration in the culture media on day 6 is a measure of the total sGAG produced by the cells over the three-day time period between media change and the sGAG measurement, and therefore is a measure of the production rate of sGAG during that time period. Data is expressed as a ratio between treated and untreated controls. Administration of LMP-1 (via AdLMP-1 at MOI 25) provided the highest sGAG level, which was 3.1±0.2 times that of the control (p<0.01). There was no significant difference in sGAG levels in media between cells treated with MOI 25 or MOI 50. Because this AdLMP-1 dose of MOI 25 was the lowest dose that could achieve the maximal sGAG response, the inventors chose MOI 25 as the working dose for the remainder of the experiments.

A time-course experiment was carried out to determine the effect of varying the length of the experiment after treatment with AdLMP-1 at MOI 25. Annulus cells were treated with LMP-1 (AdLMP-1 at MOI 25), and the production of sGAG over three day increments were measured. The results were normalized by DNA content at each time point and expressed as a ratio to untreated controls from the same time point. The sGAG level was increased to 1.6±0.2 (p<0.01) on day 3, to 2.9±0.1 (p<0.01) on day 6, and to 2.8±0.1 (p<0.01) on day 9. No increase in sGAG level was noted between day 6 and day 9, indicating that a plateau level was achieved by day 6.

LMP-1 Induction of Aggrecan Synthesis

Because aggrecan is the predominant proteoglycan of the intervertebral disc, aggrecan core protein mRNA levels were measured 6 days after treatment with AdLMP-1. Quantitative real-time PCR methods were used and the data are presented as a ratio to untreated controls. After AdLMP-1 treatment (MOI 25), aggrecan mRNA level was 2.1±0.1 (p<0.01) times that of controls. After AdLacZ treatment (MOI 25) aggrecan mRNA level was unchanged, 1.0±0.16 times that of controls. These results, together with the sGAG experiments, demonstrated that LMP-1 stimulates intervertebral disc cell production of proteoglycans.

Having established the dose and timing necessary for optimal AdLMP-1 activity on our culture system, the inventors then compared the effect of LMP-1, as administered via AdLMP-1, on annulus and nucleus cells. Rat annulus and nucleus cells were treated with AdLMP-1 at MOI 25 and the sGAG concentration of each cell type was measured on day 6. The sGAG concentration was normalized by DNA content in order to account for minor variations in cell number. The results were not normalized to untreated controls in order to compare the untreated controls of annulus and nucleus cell types. The results for untreated annulus and nucleus cells were 0.6±0.04 sGAG/DNA and 1.0±0.12 sGAG/DNA respectively. This difference was statistically significant (p<0.05) and indicated that untreated nucleus cells produce more sGAG per cell than annulus cells. After AdLMP-1 treatment the results for annulus and nucleus cells were 1.5±0.08 sGAG/DNA (p<0.01) and 2.4±0.1 sGAG/DNA (p<0.01) respectively. These values indicated statistically significant increases compared to their respective untreated controls. The relative increases from untreated to AdLMP-1 treated cells were similar between annulus and nucleus cells. The cell number at day 6 with and without AdLMP-1 treatment was determined by measuring the DNA content. The annulus cell DNA content increased 1.2 times compared to untreated controls (p<0.01), but nucleus cell DNA content was unaffected by AdLMP-1. This indicated that LMP-1 induced a mild but significant increase in the number of annulus cells but not nucleus cells.

In order to test the effect of administration of LMP-1 (via AdLMP-1) on sGAG production in vitro for a period of weeks, the inventors used an alginate culture system. Alginate provides a three-dimensional matrix for cells that is important for maintenance of chondrocytic phenotype in long term in vitro cultures. Annulus cells grown in monolayer were treated with AdLMP-1 at MOI 25 then transferred to alginate culture 24 hours later. The cells were cultured for periods of 1, 2, and 3 weeks. At 1 week, the sGAG level in the AdLMP-1 group was 1.5±0.06 (p<0.01) times that of untreated control (FIG. 5). At 2 weeks, the sGAG in the AdLMP-1 treated group increased to 2.9±0.3 (p<0.01) times that of untreated controls. This difference was maintained at 3 weeks; the sGAG level in the AdLMP-1 treated group was 2.9±0.1 (p<0.01) times that of controls. This indicated that AdLMP-1 was effective in maintaining increased sGAG accumulation in alginate for at least 3 weeks in culture.

Having demonstrated the effect of LMP-1 over-expression on proteoglycan production, we investigated the mechanism by which LMP-1 over-expression induced this effect. The time-course of changes in mRNA of over-expressed LMP-1 and BMPs (BMP-2, 4, 6, and 7) were determined. These BMPs had previously been shown to be stimulated in leukocytes and osteoblasts by LMP-1 over-expression.

The time-dependent changes in over-expressed LMP-1 after annulus cell treatment with AdLMP-1 at MOI 25 were determined. The data were expressed as a percent of the maximal mRNA level of over-expressed LMP-1 (day 6) instead of as ratio to untreated controls because no over-expressed LMP-1 mRNA was detectable in controls. LMP-1 mRNA was detectable 12 hours after treatment and continued to increase up to the last time point checked (day 6). This indicated that over-expressed LMP-1 could have an effect on downstream genes as early as 12 hours after LMP-1 administration.

The time-course of BMP mRNA levels after treatment with AdLMP-1 at MOI 25 were also determined by real-time PCR and calculated as a ratio to untreated controls at each time point. BMP-2 mRNA was upregulated early, reaching a statistically significant (p<0.01) increase at 12 hours after LMP-1 treatment. BMP-2 mRNA increase reached a plateau level by day 3. BMP-7 mRNA was upregulated later than BMP-2, reaching statistically significantly increase at day 3 (p<0.01) and day 6 (p<0.01). Neither BMP-4 nor BMP-6 mRNA levels were significantly different from those of untreated controls.

Having established that LMP-1 mRNA over-expression provides up-regulation of BMP-2 and BMP-7 mRNAs in annulus cells, the inventors tested whether this mRNA increase correlated with increased secretion of the BMP proteins into the culture media. An ELISA assay to quantitate the level of BMP-2, 4, 6, and 7 proteins in the conditioned media. Annulus cells cultured in monolayer were treated with AdLMP-1 at MOI 25. Media was changed once at day 3, and media was analyzed at day 6. Test samples therefore contained BMPs secreted during the last 3 days (day 4 to 6) of culture. Protein levels of BMP-2 and BMP-7 in the media were $3.5\pm0.4$ ($p<0.01$) and $2.5\pm0.3$ ($p<0.05$) times that of untreated controls, respectively. BMP-4 and BMP-6 protein levels were not significantly different from those of untreated control, which is consistent with the results obtained for mRNA.

Since the mRNA and protein of BMP-2 and BMP-7 were upregulated by LMP-1, the inventors investigated whether blocking these BMPs would prevent the increase in sGAG production induced by LMP-1. Annulus cells cultured in monolayer with AdLMP-1 at MOI 25 were simultaneously treated with the BMP inhibitor noggin in the culture media and the sGAG levels were measured at day 6. Cells treated with AdLMP-1 alone had increased sGAG levels ($2.7\pm0.3$ times that of untreated control), whereas cells treated with noggin at 3200 ng/ml and AdLMP-1 at MOI 25 had unchanged sGAG levels ($1.1\pm0.1$ times untreated control), indicating that noggin completely blocked the effect of AdLMP-1. Cells treated with noggin alone (3200 ng/ml) still had nearly unchanged sGAG level ($0.8\pm0.1$ times untreated control), indicating the absence of a toxic effect by noggin. The inhibitory effect of noggin on AdLMP-1 induced sGAG production was concentration dependent.

Endogenous levels of aggrecan, BMP-7, and LMP-1 mRNA in the control discs (AdGFP injected discs) were detected in the nucleus pulposus. Endogenous mRNA levels were used to calculate the increase in aggrecan, BMP-7, and LMP-1 mRNA in the AdLMP-1 injected discs. Discs injected with AdLMP-1 expressed 830% higher levels of total LMP-1 mRNA than the discs injected with AdGFP. Administration of LMP-1 via AdLMP-1 produced an 1100% increase in the BMP-7 mRNA level over control ($p<0.05$). Aggrecan mRNA level was increased by 66% over control ($p<0.05$).

Endogenous levels of BMP-2, BMP-7, LMP-1, and aggrecan mRNA were also detected. A correlation between increasing AdLMP-1 dose and total LMP-1 mRNA was seen. Administration of LMP-1 via AdLMP-1 significantly increased BMP-2 and BMP-7 mRNA levels maximally at a dose of $10^7$ pfu per disc ($p<0.05$) AdLMP-1 at a dose of $10^7$ pfu per disc led to the highest increase in aggrecan mRNA, 50% over control ($P<0.05$).

Administration LMP-1 to intervertebral disc cells resulted in an increase in sGAG production and an increase in aggrecan mRNA levels. LMP-1 administration produced an increase in the mRNA and protein levels of BMP-2 and BMP-7 in vitro, and the effect of LMP-1 administration on upregulation of proteoglycan production could be blocked by administration of the BMP inhibitor noggin.

Sprague-Dawley rats aged 11 months were euthanized and intervertebral disc tissue from the lumbar spine and tail were harvested in under sterile conditions. Annulus fibrosus and nucleus pulposus were separately dissected and diced. The intervertebral disc tissue was placed in Dulbecco's modified Eagle's medium and Ham's F12 medium (DMEM/F-12; GIBCO BRL, Grand Island, N.Y., U.S.A.) containing 100 unit/ml penicillin and 100 mg/ml streptomycin. The intervertebral disc tissue was treated with 0.2% pronase (Sigma Chemical, St. Louis, Mo., U.S.A.) in the medium for 1 hour at 37° C. and then treated with 0.025% collagenase (Sigma Chemical, St. Louis, Mo., U.S.A.) for 6 hours at 37° C. Isolated cells were washed and filtered through a 70 mm mesh (Falcon, Franklin Lakes, N.J., U.S.A.) into 75 cm² flasks with 12 ml DMEM/F-12 medium containing 10% fetal bovine serum (FBS), 100 unit/ml penicillin, 100 mg/ml streptomycin, 2 mM L-glutamine and 50 mg/ml ascorbate. The cells were grown at 37° C. in 5% $CO_2$ with humidification. The culture media was changed every 2 days for approximately 8 days.

Two different viruses were used. The replication deficient type 5 Adenovirus containing the human LMP-1 cDNA driven by a CMV promoter (AdLMP-1) was used as the experimental virus. The control virus consisted of a similar replication deficient type 5 adenovirus containing the lacZ cDNA.

When the primary culture of intervertebral disc cells became confluent, the cells were subcultured into 6-well plates at 400,000 cells per well. Three days later, the cells were treated with adenovirus containing the cDNA for either the human LMP-1 gene (AdLMP-1) or the LacZ gene (AdLacZ). Cell number was determined at day 0 by counting a control well using a hemocytometer. The viral dose was expressed as a multiplicity of infection (MOI), the number of plaque-forming unit (pfu) per cell. This is essentially the number of recombinant adenoviral plaque-forming units to which a single intervertebral disc cell was exposed. The cultured cells were treated for thirty minutes at 37° C. with AdLMP-1 or AdLacZ in 300 ml of DMEM/F-12 with 0% FBS at different MOIs (0, 10, 25, 50) as designated in each experiment. Then the culture volume was raised to 2.0 ml with DMEM/F-12 medium containing 1% FBS, 100 unit/ml penicillin, 100 mg/ml streptomycin, 2 mM L-glutamine and 50 mg/ml Vitamin C. The medium was changed every 3 days during the experiment.

The sulfated-glycosaminoglycan (sGAG) content of the culture media was assayed using the 1,9-dimethylmethylene blue (DMMB) method. The culture media 2 ml was centrifuged (5000×G for 30 minutes) to concentrate the sGAG using the Centricon YM-50 centrifugal filter (Millipore Co., Bedford, Mass., U.S.A.). The sample solution (20 ml) were mixed gently with 200 ml DMMB dye solution in a 96-well microtiter plate, and the optical density (OD) was checked immediately at 520 nm wavelength filter. A standard curve was constructed using serial dilutions of chondroitin sulfate (Sigma Chemical, St. Louis, Mo., U.S.A.). Total sGAG in the media were normalized by DNA content and presented as a ratio to the untreated control.

The cell number was determined by the DNA content of each well, and DNA content was measured with a Hoechst dye 33258 (Polysciences, Warrington, Pa., U.S.A.) method, as previously described. Cultured cells were removed from the plate by exposure to papain (10 units/ml). Cells were then pelleted and incubated at 60° C. for 3 hours. A twenty microliter aliquot of the papain digest was mixed with 200 ml of Hoechst dye 33258 solution in a 96-well fluoroplate. Emission and excitation spectra were measured in Luminescence Spectrometer LS 50B (Perkin-Elmer, Wellesly, Mass., U.S.A.) at 456 nm and 365 nm, respectively. Standard curves were generated at the time of each measurement using known concentrations of calf thymus DNA (Sigma Chemical, St. Louis, Mo., U.S.A.).

Alginate bead cultures are useful for maintaining chondrocytic phenotype in long term cultures. This method was to determine the effect of AdLMP-1 in three week cultures. The cells were treated in monolayer cultures as described above. One day later, the cells were released by trypsinization and washed 2 times with media. The isolated cells were resuspended in 0.6% low-viscosity sterile alginate (Sigma Chemical, St. Louis, Mo., U.S.A.) solution at 600,000 cells/ml. The cells were dispensed into a 0.102M CaCl+0.15M NaCl solution in a dropwise fashion through a 21-gauge needle attached to 10-ml plastic syringe in order to form the alginate beads. After 10 minutes the newly formed beads (containing approximately 12,000 cells/bead) were washed three times with sterile 0.9% NaCl solution followed by two washes with DMEM/F-12. The beads containing the annulus fibrosus cells were separately cultured in 6 wells plate with DMEM/F-12 medium containing 1% FBS, 100 unit/ml penicillin, 100 mg/ml streptomycin, 2 mM L-glutamine and 50 mg/ml Vitamin C. The media was changed every two days for different time periods (1, 2, and 3 weeks). The alginate beads were dissolved in 350 ml sodium citrate buffer (55 mmol/L Na-citrate, 50 mmol/L EDTA, 150 mmol/L NaCl, pH7.4). Cells were pelleted with centrifugation and the sGAG content in the dissolved solution was measured with the DMMB method described above. The sGAG content that remained the cell pellet was negligible compared to that in the suspension. The results were described as fold increase over untreated control group using sGAG of dissolved solution.

Quantification of mRNA Levels.

Real-time PCR was used to determine mRNA levels of BMP-2, BMP-4, BMP-6, BMP-7, and over-expressed LMP-1 in a quantitative fashion. The primers for all of the genes were validated by determining the product size on an agarose gel and by DNA sequencing the amplicon. 18S levels were determined in each sample to use as an internal control.

Total RNA of each sample was extracted by a single-step method using a guanidium thiocyanate-phenol-chloroform technique. The concentration of the isolated RNA was determined with a spectrophotometer (DU-500; Beckman, Fullerton, Calif., U.S.A.) at 260 nm wavelength. The RNA was treated with DNAse 1 (Ambion, Inc. Texas, U.S.A.) to remove DNA contamination of the samples. Reverse transcription was carried out in 40 ml volume with 2 mg of total RNA; 30 U Avian Myeloblastosis virus reverse transcriptase (Promega, Madison, Wis., U.S.A.); 5 mM of $MgCl_2$; 60 U/ml of RNAsin (Promega, Madison, Wis., U.S.A.); 1 mM of each deoxyadenosine triphosphate (dATP), deoxycytidine triphosphate (dCTP), deoxyguanidine triphosphate (dGTP), deoxythymidine triphosphate (dTTP); and 1 mg oligo$(dT)_{15}$ primer for 45 minutes at 42° C. PCR was performed for 30 cycles (95° C., 30"; 62° C., 30"; 72° C., 45") with Amplitaq® DNA polymerase. To confirm the absence of DNA contamination, RNA samples treated without reverse transcriptase were also subjected to PCR: the absence of PCR product confirmed the lack of DNA contamination.

Real-time PCR has been reported to be a rapid, reliable, and reproducible method for quantitative detection of specific mRNAs. A real-time PCR method using SYBR® Green Real-Time PCR Kit (Applied Biosystems, Foster City, Calif., U.S.A.) was used to perform quantitative mRNA analysis of BMP-2, BMP-4, BMP-6, BMP-7, and aggrecan. Twenty-five microliters (25 ml) of reaction volume included 5 ml of cDNA, 3.75 picomole of each primer (BMP-2, -4, -6, -7 and 18S), and 12.5 ml of SYBR® Green master mix (2×, Biorad, Hercules, Calif., U.S.A.). To quantify mRNA levels of overexpression LMP-1 and 18S, real-time PCR method using TaqMan® Real-Time PCR Kit (Applied Biosystems, Foster City, Calif., U.S.A.) was also performed. Twenty-five microliters (25 ml) of reaction volume included 5 ml of cDNA, 3.75 pmol of each primer, and 12.5 ml of TaqMan® PCR master mix (2×, Biorad, Hercules, Calif., U.S.A.).

Real-time PCR was performed with the following 3 step protocol; step 1: 50° C. for 2 minutes, step 2: 95° C. for 10 minutes, and step 3: (95° C. for 15 seconds, 60° C. for 1 minute)×45 cycles using the GeneAmp®; 5700 Sequence Detection system (Applied Biosystems, Foster City, Calif., U.S.A.). To confirm amplification specificity, the PCR products were subjected to a dislocation curve analysis. Threshold cycles (Ct) of each reaction were standardized according to 18S using the comparative-$^{\Delta\Delta}Ct$ method, as described previously.

ELISA Assay for BMP 2, 4, 6 and 7

Standard curves of BMPs were constructed using increasing concentrations (0.1 ng/100 μL per well to 1000 ng/100 μL per well) of human BMP 2, 4, 6, and 7 (Genetics Institute, Cambridge, Mass.) dissolved in 0.05 mol/L bicarbonate buffer. One hundred microliters of the samples were added to each well in triplicate. After incubating overnight at 4° C., the plates were washed with 0.01 M phosphate-buffered saline with 0.5% Tween 20 (PBST) three times and unreacted sites were blocked with 1% bovine albumin (Sigma, ST. Louis, Mo.) at room temperature for 1 hour. After the plates were washed with PBST, primary antibody (1:1000) was added to each well in 100 microliter aliquots and incubated at room temperature for 2 hours. Polyclonal goat antibodies to BMP 2, 4, and 6 (Santa Cruz Inc, Santa Cruz, Calif.) and rabbit antibody to BMP 7 (Sigma, St. Louis, Mo.) were used. The plates were washed with PBST and then incubated respectively with alkaline phosphatase conjugated anti-goat IgG and anti-rabbit IgG (Sigma, St. Louis, Mo.) at room temperature for 1 hour. Color was developed with the substrate p-nitrophenyl phosphate (Sigma, St. Louis, Mo.) for 20 minutes before the reaction was stopped with 3N NaOH. The color was quantified by measuring the absorption difference at 405 nm using an $EI_x$ 800-microplate reader (Bio-Tek Instruments, Winooska, Vt.).

To quantitate the results, linear regression plots were made for each standard. In all cases, the concentrations of samples were extrapolated from the linear regression plots of the standard in according to the corresponding values at the same absorbance as the standards.

BMP Inhibition by Noggin Glycoprotein

Noggin is a glycoprotein that binds to BMP-2, 4, 6, and 7 in a highly specific manner and prevents these BMPs from activating their cognate receptors. A form of mouse noggin (noggin-FC Sigma Chemical, St. Louis, Mo., U.S.A.) was used in experiments to determine the effect of specifically blocking BMPs after AdLMP-1 treatment. Noggin at different concentrations (100, 200, 400, 800, 1600 and 3200 ng/ml) was applied to cells on day 0 and day 3 after AdLMP-1 (MOI 25) treatment. On day 6, the conditioned media were assayed to examine sGAG production using the DMMB method described above. Results indicated that LMP-1 effects could be blocked by administration of Noggin, demonstrating that LMP-1 activity is, in part, related to its induction of BMPs.

What is claimed is:

1. A method of inducing bone formation in a mammal comprising administering an effective amount of a fusion polypeptide consisting of a protein transduction domain and an amino acid sequence selected from the group consisting of the amino acid sequence consisting of SEQ ID NO 1, the amino acid sequence consisting of SEQ ID NO 2, the amino acid sequence consisting of SEQ ID NO 4, the amino acid sequence consisting of SEQ ID NO 7, and the amino acid sequence consisting of SEQ ID NO 8.

2. The method of claim 1 wherein the protein transduction domain is chosen from the group consisting of HIV-TAT, VP-22, a growth factor signal peptide sequence, Pep-i, and a *Drosophila* Antp peptide.

3. The method of claim 1 wherein the protein transduction domain is an HIV-TAT protein transduction domain.

4. The method of claim 1 wherein the fusion polypeptide is administered as an implant.

5. The method of claim 1 wherein the fusion polypeptide is administered by hydrogel.

6. The method of claim 1 the fusion polypeptide is administered to at least one multipotent progenitor cell.

7. The method of claim 6 wherein the at least one multipotent progenitor cell is implanted into the mammal.

8. A method of inducing proteoglycan synthesis in a mammal comprising administering an effective amount of a fusion polypeptide consisting of a protein transduction domain and an amino acid sequence selected from the group consisting of the amino acid sequence consisting of SEQ ID NO 1, the amino acid sequence consisting of SEQ ID NO 2, the amino acid sequence consisting of SEQ ID NO 4, the amino acid sequence consisting of SEQ ID NO 7, and the amino acid sequence consisting of SEQ ID NO 8, wherein the proteoglycan concentration prior to said administering step is less than said concentration post said administering step.

9. The method of claim 8 wherein the protein transduction domain is chosen from the group consisting of HIV-TAT, VP-22, a growth factor signal peptide sequence, Pep-1, and a *Drosophila* Antp peptide.

10. The method of claim 8 wherein the protein transduction domain is an HIV-TAT protein transduction domain.

11. The method of claim 8 wherein the fusion polypeptide is administered as an implant.

12. The method of claim 8 wherein the fusion polypeptide is administered by hydrogel.

13. The method of claim 8 wherein the fusion polypeptide is administered to at least one multipotent progenitor cell.

14. The method of claim 13 wherein the at least one multipotent progenitor cell is implanted into the mammal.

15. The method of claim 8 wherein the proteoglycan is aggrecan.

16. A method of inducing osteoblast differentiation in a progenitor cell, the method comprising administering to the progenitor cell an effective amount of a fusion polypeptide consisting of a protein transduction domain and an amino acid sequence selected from the group consisting of the amino acid sequence consisting of SEQ ID NO 1, the amino acid sequence consisting of SEQ ID NO 2, the amino acid sequence consisting of SEQ ID NO 4, the amino acid sequence consisting of SEQ ID NO 7, the amino acid sequence consisting of SEQ ID NO 8, wherein the differentiated osteoblast concentration prior to said administering step is less than said concentration post said administering step.

17. The method of claim 16 wherein the protein transduction domain is chosen from the group consisting of HIV-TAT, VP-22, a growth factor signal peptide sequence, Pep-1, and a *Drosophila* Antp peptide.

18. The method of claim 16 wherein the protein transduction domain is an HIV-TAT protein transduction domain.

19. The method of claim 16 wherein the fusion polypeptide is administered as an implant.

20. The method of claim 16 wherein the fusion polypeptide is administered by hydrogel.

21. The method of claim 16 wherein the fusion polypeptide is administered to at least one multipotent progenitor cell.

22. The method of claim 21 wherein the at least one multipotent progenitor cell is implanted into the mammal.

* * * * *

UNITED STATES PATENT AND TRADEMARK OFFICE
CERTIFICATE OF CORRECTION

| | | |
|---|---|---|
| PATENT NO. | : 7,892,532 B2 | Page 1 of 1 |
| APPLICATION NO. | : 10/806915 | |
| DATED | : February 22, 2011 | |
| INVENTOR(S) | : Titus et al. | |

It is certified that error appears in the above-identified patent and that said Letters Patent is hereby corrected as shown below:

On the Face Page, in Field (73), under "Assignee" in Column 1, Lines 1-2, delete "In Emory University" and insert -- Inc., Warsaw, IN (US) --, therefor.

In Column 1, Line 14, after "30," delete "[1997]".

In Column 5, Line 11, delete "HLPM is" and insert -- HLMP-ls --, therefor.

In Column 5, Line 57, delete "4)" and insert -- 4, --, therefor.

In Column 9, Line 2, delete "Schwarze." and insert -- Schwarze --, therefor.

In Column 11, Line 42, after "utilizing" delete "10".

In Column 11, Line 42, delete "pcDNA3.1" and insert -- pCDNA3.1 --, therefor.

In Column 11, Line 57, delete "pcDNA3.1" and insert -- pCDNA3.1 --, therefor.

In Column 17, Line 51, delete "(P<0.05)." and insert -- (p<0.05). --, therefor.

In Column 25, Line 43, in Claim 1, delete "Pep-i," and insert -- Pep-1, --, therefor.

Signed and Sealed this
Nineteenth Day of April, 2011

David J. Kappos
*Director of the United States Patent and Trademark Office*

SEQUENCE LISTING

<160> NUMBER OF SEQ ID NOS: 13

<210> SEQ ID NO 1
<211> LENGTH: 22
<212> TYPE: PRT
<213> ORGANISM: Homo sapiens

<400> SEQUENCE: 1

Ala Pro Ser Val Ser Leu Asn Lys Thr Ala Arg Pro Phe Gly Ala Pro
 1               5                  10                  15

Pro Pro Ala Asp Ser Ala
            20

<210> SEQ ID NO 2
<211> LENGTH: 22
<212> TYPE: PRT
<213> ORGANISM: Homo sapiens

<400> SEQUENCE: 2

Ala Arg Pro Phe Gly Ala Pro Pro Ala Asp Ser Ala Pro Gln Gln
 1               5                  10                  15

Asn Gly Gln Pro Leu Arg
            20

<210> SEQ ID NO 3
<211> LENGTH: 22
<212> TYPE: PRT
<213> ORGANISM: Homo sapiens

<400> SEQUENCE: 3

Lys Pro Gln Lys Ala Ser Ala Pro Ala Ala Asp Pro Pro Arg Tyr Thr
 1               5                  10                  15

Phe Ala Pro Ser Val Ser
            20

<210> SEQ ID NO 4
<211> LENGTH: 22
<212> TYPE: PRT
<213> ORGANISM: Homo sapiens

<400> SEQUENCE: 4

Leu Asn Lys Thr Ala Arg Pro Phe Gly Ala Pro Pro Ala Asp Ser
 1               5                  10                  15

Ala Pro Gln Gln Asn Gly
            20

<210> SEQ ID NO 5
<211> LENGTH: 40
<212> TYPE: PRT
<213> ORGANISM: Homo sapiens

<400> SEQUENCE: 5

Ala Ser Ala Pro Ala Ala Asp Pro Pro Arg Tyr Thr Phe Ala Pro Ser
 1               5                  10                  15

Val Ser Leu Asn Lys Thr Ala Arg Pro Phe Gly Ala Pro Pro Ala
            20                  25                  30

Asp Ser Ala Pro Gln Gln Asn Gly
        35                  40

<210> SEQ ID NO 6

```
<211> LENGTH: 45
<212> TYPE: PRT
<213> ORGANISM: Homo sapiens

<400> SEQUENCE: 6

Ser Lys Pro Gln Lys Ala Ser Ala Pro Ala Ala Asp Pro Pro Arg Tyr
1               5                   10                  15

Thr Phe Ala Pro Ser Val Ser Leu Asn Lys Thr Ala Arg Pro Phe Gly
            20                  25                  30

Ala Pro Pro Pro Ala Asp Ser Ala Pro Gln Gln Asn Gly
        35                  40                  45

<210> SEQ ID NO 7
<211> LENGTH: 30
<212> TYPE: PRT
<213> ORGANISM: Homo sapiens

<400> SEQUENCE: 7

Gly Ala Pro Pro Pro Ala Asp Ser Ala Pro Gln Gln Asn Gly Gln Pro
1               5                   10                  15

Leu Arg Pro Leu Val Pro Asp Ala Ser Lys Gln Arg Leu Met
            20                  25                  30

<210> SEQ ID NO 8
<211> LENGTH: 30
<212> TYPE: PRT
<213> ORGANISM: Homo sapiens

<400> SEQUENCE: 8

Gly Ala Pro Pro Pro Ala Asp Ser Ala Pro Gln Gln Asn Gly Cys Arg
1               5                   10                  15

Pro Leu Thr Asn Ser Arg Ser Asp Arg Trp Ser Gln Met Pro
            20                  25                  30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tcctcatccg ggtcttgcat gaactcggtg                                          30

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcccccgccc gctgacagcg ccccgcaa                                            28

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
```

```
ccatggattc cttcaaagta gtgc                                          24

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cagggcgggc ggctggtag                                                19

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6-His tag

<400> SEQUENCE: 13

His His His His His His
 1               5
```